United States Patent
Jandke et al.

(10) Patent No.: US 8,101,789 B2
(45) Date of Patent: Jan. 24, 2012

(54) METHOD FOR THE PRODUCTION OF POLYMERIZABLE SILICONES

(75) Inventors: Markus Jandke, Burgkirchen (DE); Florian Koopmann, Burghausen (DE); Birgit Peschanel, Burghausen (DE)

(73) Assignee: Wacker Chemie AG, Munich (DE)

( * ) Notice: Subject to any disclaimer, the term of this patent is extended or adjusted under 35 U.S.C. 154(b) by 383 days.

(21) Appl. No.: 12/521,915

(22) PCT Filed: Jan. 8, 2008

(86) PCT No.: PCT/EP2008/050109
§ 371 (c)(1),
(2), (4) Date: Jul. 1, 2009

(87) PCT Pub. No.: WO2008/090012
PCT Pub. Date: Jul. 31, 2008

(65) Prior Publication Data
US 2010/0041909 A1    Feb. 18, 2010

(30) Foreign Application Priority Data

Jan. 24, 2007 (DE) .................. 10 2007 003 578

(51) Int. Cl.
*C07F 7/08* (2006.01)
*C08G 77/00* (2006.01)
(52) U.S. Cl. ........ 556/458; 556/450; 556/451; 556/453; 556/457
(58) Field of Classification Search .................. None
See application file for complete search history.

(56) References Cited

FOREIGN PATENT DOCUMENTS

| EP | 1510520 A | 3/2005 |
|---|---|---|
| EP | 1472264 B | 6/2005 |
| JP | 11217389 A | 8/1999 |
| JP | 2000186095 A | 7/2000 |
| WO | 03064436 A | 8/2003 |

*Primary Examiner* — Daniel Sullivan
*Assistant Examiner* — Yevegeny Valenrod
(74) *Attorney, Agent, or Firm* — Brooks Kushman P.C.

(57) ABSTRACT

Siloxy-substituted silane-containing polymerizable silicones are prepared in high purity by metering a substituted alkoxysilane into a mixture of disiloxane, acetic acid, and acid catalyst, adding acetyl chloride, separating an acidic phase from a product phase, and adding hexamethyldisilazane to the product phase, which is then distilled.

10 Claims, No Drawings

METHOD FOR THE PRODUCTION OF POLYMERIZABLE SILICONES

CROSS-REFERENCE TO RELATED APPLICATION

This application is the U.S. national phase of PCT Appln. No. PCT/EP2008/050109 filed Jan. 8, 2008 which claims priority to German application DE 10 2007 003 578.2 filed Jan. 24, 2007.

BACKGROUND OF THE INVENTION

1. Field of the Invention

The invention relates to the production of polymerizable silicones comprising siloxy-substituted silane structures. In particular, the invention relates to the production of silanes of high purity having polymerizable groups and substituted with triorganosiloxy groups by substitution of alkoxysilanes with disiloxanes.

2. Description of the Related Art

Polymerizable silicones, such as 3-acryloxypropyltris(trimethylsiloxy)silane, 3-methacryloxypropyltris(trimethylsiloxy)silane, 3-methacryloxypropyltris(di-methylphenylsiloxy)silane, 1-methacryloxymethyltris(trimethylsiloxy) silane, etc. are useful as a raw material or monomer for the production of electronic materials, for the production of contact lenses, as raw material in compositions for functional and industrial coatings, polymeric microstructures or cosmetic applications. The use of polymerizable silicones for these uses requires the provision of high-purity materials with a reduced content of by-products such as monohydroxysilanes, monoorganooxysilanes and difunctional disiloxanes, as well as inorganic and metallic impurities.

JP 11-217389 describes a method in which an alkoxy- or aryloxy-substituted silane (e.g. 3-methacryloxypropyltrimethoxysilane) is reacted with hexamethyldisiloxane in the presence of a carboxylic acid (e.g. acetic acid) and an acidic catalyst (trifluoromethanesulfonic acid), giving a siloxy-substituted product. The method is preferably performed such that hexamethyldisiloxane, carboxylic acid and catalyst are initially introduced before the alkoxy or aryloxy component is added, and the reaction is carried out at ca. 20-70° C. By adding a small amount of hexamethyldisilazane (0.0025 mol per mole of alkoxysilane), the reaction is halted and neutralized, giving a product with reduced purity (<90 area %). The ratio of product G-Si(OSiMe$_3$)$_3$ [G=methacryloxypropyl] to the monoorganoxy by-product G-Si(OMe)(OSiMe$_3$)$_2$ is ca. 8.3 (i.e. ca. 10.7% monoorganoxy by-product). The ratio of product to the difunctional by-product G-[Me$_3$SiO]$_2$Si—O—Si[OSiMe$_3$]$_2$-G is 54.9 (i.e. ca. 1.8% difunctional disiloxane). JP 11-217389 describes how the condensation of silanol groups present to difunctional disiloxane is suppressed through appropriate temperature control, but not how the content of monohydroxysilane (silanol) can be limited. The high content of impurities is problematic with regard to the aforementioned applications.

From JP 2000-186095 it is known to react hexamethyldisiloxane, a carboxylic acid (acetic acid) and a strong acid (concentrated sulfuric acid) with 3-methacryloxypropyltrimethoxysilane, the latter preferably being added at a temperature of from −10° C. to 0° C. over the course of 30 min. Following post reaction, washing with water, and distillation, 3-methacryloxypropyltris(trimethylsiloxy) silane is obtained with a purity of 90.2-97.8%. The product is contaminated with monohydroxy by-product and dimer by-product (difunctional disiloxane). Besides the high content of the specified impurities (in particular difunctional disiloxane), a considerable disadvantage of the method is that following the actual reaction, a lengthy and therefore uneconomical aging of the reaction mixture at various temperatures over a period of 24 h has to be accepted. The aging process is an essential part of the method since during the reaction monohydroxy by-products are formed whose content is reduced in the course of the aging process by converting the silanols into difunctional disiloxane via a dehydrogenation. In this connection, contents of difunctional disiloxane up to 10% are obtained, which is unacceptable for a number of applications.

EP 1510520 A describes the production of high-purity branched siloxanes with a reduced content of monoorganoxysilane or monohydroxysilane impurities in a two-stage process via the post-reaction of a contaminated crude product (following complete or following partial work-up and/or isolation) with disiloxane and acid in high yield. However, the cited method has the disadvantage that, first, on account of the aqueous work-up, monohydroxysilane and/or monoorganoxy impurities can still continue to form in the acidic medium. The after-treatment can reduce the content of monoorganoxysilane or monohydroxysilane contamination. Second, an essential disadvantage of the method is that prior to the post-reaction, the crude product must be worked up completely or at least partially and that consequently the washings, phase separations (and optionally also distillations) are carried out twice.

EP 1472264 A describes a method for the production of high-purity silicone compounds via the substitution of alkoxy, aryloxy or acyloxy groups by trialkylsiloxy units. The reaction is started by adding an alkoxy- or aryloxysilane, in the presence of a carboxylic acid (acetic acid), an acidic catalyst (CF$_3$SO$_3$H), a disiloxane (Me$_3$SiOSiMe$_3$).

For example, 3-methacryloxypropyltris(trimethylsiloxy) silane is obtained in high yield with a purity of 98.7%, the impurities obtained being 1.3% disiloxane (dimer) and less than 0.5% of the monoorganoxysilane by-product CH$_2$=CH(CH$_3$)COO—(CH$_2$)$_3$—Si(OMe)(OSiMe$_3$)$_3$. For further products, considerably lower purities (down to 93%) and higher contents of dimeric compounds (up to 4.4%) are measured. However, EP 1472264 does not describe how the content of monohydroxysilane by-product can be kept low until isolation of the product and how its formation can be prevented in the course of the work-up/neutralization.

Besides the high required amount of carboxylic anhydride, an essential disadvantage of the cited method is that the content of difunctional impurities (disiloxane) is furthermore above 1% and upon dispensing with a distillation, also inorganic and polymeric organic impurities are said to be present. In the case of a distillation, a significantly lower yield would be expected. Especially for the production of electronic and optical media and components, for the production of contact lenses and also for use in functional coatings, a markedly lower content of difunctional impurities is required. In these applications, in particular the content of difunctional silicones in the polymerizable silicone is troublesome since it triggers, by increasing the crosslinking density, a modification of the mechanical and thus also of the optical properties and/or of the desired properties for use in the sector of electronic materials or functional coatings. Residual contents of monohydroxy and monomethoxy impurities can lead in these applications, as a result of cleavage reaction and/or condensation reactions, to an adverse change in the functional properties of the materials, components or coatings. Residual contents of inorganic salts or polymeric fractions can lead to undesired light scattering and inadequate performance of optical components. In electronic materials, in this case a significant change in the insulation effect/conductivity and the breakdown field strength is to be expected. Surface properties of functional coatings can be lastingly adversely affected by these impurities. It is therefore essential that polymerizable silicones are made available in high-purity form with a minimum content of difunctional silicones, further condensable silicones and also inorganic impurities.

SUMMARY OF THE INVENTION

It was an object of the invention to provide a method for the production of polymerizable silicones of high purity in which the disadvantages described above are avoided, and in which polymerizable silicones of high purity with a content of at least 98.5% are obtained which have, as by-products, a content of less than 0.4% of difunctional disiloxane and of less than 0.4% each of monohydroxy and/or monoalkoxy structures. These and other objects are achieved by the invention, wherein disiloxane is reacted with substituted alkoxysilane in the presence of acetic acid and an acidic catalyst, following post reaction adding acetyl chloride, separating an acidic phase, and treating the organic phase with hexamethyl disilazane.

DETAILED DESCRIPTION OF THE PREFERRED EMBODIMENTS

The invention thus provides a method for the production of high-purity polymerizable silicones of the formula $$P\text{—}Y\text{-Sp-Si}(R^2)_n(OSiR^1_3)_{(3-n)} \qquad (I)$$

by
(a) initially introducing disiloxane (1) of the formula $$(R^1)_3SiOSi(R^1)_3 \qquad (II)$$

in the presence of acetic acid (2) and acidic catalyst (3),
(b) at a temperature of from 0° to 60° C., metering in a substituted alkoxysilane (4) of the formula $$P\text{—}Y\text{-Sp-Si}(R^2)_n(OR^3)_{(3-n)} \qquad (III),$$

over the course of 0.5 h-3 h and then post-reacting the mixture at 0°-60° C. over the course of 0.5 h to 3 h,
(c) adding 0.2-1.0 mol of acetyl chloride (5), based on 1 mol of alkoxysilane (4),
(d) following phase separation, separating off an acid phase (lower layer),
(e) adding 0.02-1.0 mol of hexamethyldisilazane (6), based on 1 mol of alkoxysilane (4),
(f) after filtering off the resulting salt
removing the readily volatile constituents and distilling the product, and optionally
(g) then filtering the product,
where
$R^1$ is identical or different and is a hydrogen atom or an optionally substituted monovalent hydrocarbon radical having 1 to 18 carbon atoms,
$R^2$ is identical or different and is a hydrogen atom or an optionally substituted monovalent hydrocarbon radical having 1 to 18 carbon atoms,
$R^3$ is identical or different and is an alkyl radical having 1 to 18 carbon atoms which is optionally substituted with alkoxy groups,
Sp is a single bond or a divalent hydrocarbon radical having 1 to 8 carbon atoms,
Y is a single bond or —O—,
P is an acryloxy, methacryloxy, vinyl or allyl radical,
n is 0, 1 or 2, preferably 0.

The invention further provides high-purity polymerizable silicones of the formula $$P\text{—}Y\text{-Sp-Si}(R^2)_n(OSiR^1_3)_{(3-n)} \qquad (I)$$

which have a purity of at least 98.5%, preferably at least 99.0%,
a content of less than 0.4%, preferably less than 0.2%, of difunctional disiloxane of the formula $$[P\text{—}Y\text{-Sp-Si}(R^2)_n(OSiR^1_3)_{(2-n)}]_2O,$$

of less than 0.4%, preferably less than 0.3%, of monohydroxysilane of the formula $$P\text{—}Y\text{-Sp-Si}(R^2)_n(OH)(OSiR^1_3)_{(2-n)}$$

and less than 0.4%, preferably less than 0.3%, of monoalkoxysilane of the formula $$P\text{—}Y\text{-Sp-Si}(R^2)_n(OR^3)(OSiR^1_3)_{(2-n)},$$

where $R^1$, $R^2$, $R^3$, Sp, Y, P and n have the meaning given above.

Examples of $R^1$ are alkyl, alkenyl, alkynyl and aryl radicals having 1-18 carbon atoms, preferably 1-15 carbon atoms, and more preferably 1-9 carbon atoms. Examples of $R^1$ are alkyl radicals such as the methyl, ethyl, n-propyl, isopropyl, n-butyl, isobutyl, tert-butyl, n-pentyl, n-hexyl and n-octyl radicals; cycloalkyl radicals such as the cyclopentyl and cyclohexyl radicals; alkenyl and alkynyl radicals such as the vinyl, propenyl, allyl and ethinyl radicals; and aryl radicals such as the phenyl radical.

Examples of $R^2$ are alkyl, alkenyl, alkynyl and aryl radicals having 1-18 carbon atoms, preferably 1-9 carbon atoms, and more preferably 1-6 carbon atoms. Examples of $R^2$ are alkyl radicals such as the methyl, ethyl, n-propyl, isopropyl, n-butyl, isobutyl, tert-butyl, n-pentyl, n-hexyl and n-octyl radicals; cycloalkyl radicals such as the cyclopentyl and cyclohexyl radicals; alkenyl and alkynyl radicals such as the vinyl, propenyl, allyl and ethinyl radicals; and aryl radicals such as the phenyl radical.

Examples of $R^3$ are alkyl radicals having 1 to 3 carbon atoms optionally substituted with alkoxy groups. Examples of $R^3$ are the methyl, ethyl, and propyl radicals.

Examples of Sp are alkylene or cycloalkylene radicals, such as —CH$_2$—, —CH$_2$—CH$_2$— and —CH$_2$—CH$_2$—CH$_2$— radicals and C$_4$-C$_8$-alkylene radicals and cyclohexylene radicals.

Y is preferably —O—.
P is preferably an acryloxy or methacryloxy radical.
Examples of disiloxanes of the formula $(R^1)_3SiOSi(R^1)_3$ are
hexamethyldisiloxane,
hexaethyldisiloxane,
1,3-di-tert-butyl-1,1,3,3-tetramethyldisiloxane,
1,1,3,3-tetramethyldisiloxane,
1,3-divinyl-1,1,3,3-tetramethyldisiloxane and
1,3-diphenyl-1,1,3,3-tetramethyldisiloxane.
Examples of alkoxysilanes are:
1-acryloxymethyltrimethoxysilane,
2-acryloxyethyltrimethoxysilane,
3-acryloxypropyltrimethoxysilane,
1-methacryloxymethyltrimethoxysilane,
1-methacryloxymethyldimethoxymethylsilane,
2-methacryloxyethyltrimethoxysilane,
3-methacryloxypropyltrimethoxysilane,
1-acryloxymethyltriethoxysilane,
2-acryloxyethyltriethoxysilane,
3-acryloxypropyltriethoxysilane,
1-methacryloxymethyltriethoxysilane, 2-methacryloxyethyltriethoxysilane,
3-methacryloxypropyltriethoxysilane,
4-methacryloxybutyltrimethoxysilane,
6-methacryloxyhexyltrimethoxysilane,
8-methacroloxyoctyltrimethoxysilane,
methacryloxycyclohexyltrimethoxysilane, and
vinyltrimethoxysilane.

The alkoxysilanes used are already substituted with one polymerizable group. In order to avoid a polymerization of the polymerizable group, it is also possible to use alkoxysilanes which are already provided with a low content of a stabilizer.

Alternatively, a stabilizer can be added to the reaction mixture (0-5000 ppm, preferably 0-3000 ppm, based on alkoxysilane used). Examples of stabilizers are 2,6-di-tert-butyl-4-methylphenol (BHT), 2,6-di-tert-butyl-4-(dimethylaminomethyl)phenol and phenothiazine.

Particularly preferred alkoxysilanes are:
3-methacryloxypropyltrimethoxysilane,
1-methacryloxymethyltrimethoxysilane,
1-methacryloxymethyldimethoxymethylsilane, and
vinyltrimethoxysilane.

Examples of polymerizable silicones of the formula P—Y-Sp-Si($R^2$)$_n$(OSi$R^1_3$)$_{(3-n)}$ are
1-acryloxymethyltris(trimethylsiloxy)silane,
2-acryloxyethyltris(trimethylsiloxy)silane,
3-acryloxypropyltris(trimethylsiloxy)silane,
1-methacryloxymethyltris(trimethylsiloxy)silane,
2-methacryloxyethyltris(trimethylsiloxy)silane,
3-methacryloxypropyltris(trimethylsiloxy)silane,
4-methacryloxybutyltris(trimethylsiloxy)silane,
6-methacryloxyhexyltris(trimethylsiloxy)silane,
8-methacryloxyoctyltris(trimethylsiloxy)silane,
methacryloxycyclohexyltris(trimethylsiloxy)silane,
1-acryloxymethylbis(trimethylsiloxy)methylsilane,
2-acryloxyethylbis(trimethylsiloxy)methylsilane,
3-acryloxypropylbis(trimethylsiloxy)methylsilane,
1-methacryloxymethylbis(trimethylsiloxy)methylsilane,
2-methacryloxyethylbis(trimethylsiloxy)methylsilane,
3-methacryloxypropylbis(trimethylsiloxy)methylsilane,
1-methacryloxymethyltris(dimethylvinylsiloxy)silane,
3-methacryloxypropyltris(dimethylvinylsiloxy)silane, and
vinyltris(trimethylsiloxy)silane.

Preferred examples of polymerizable compounds P—Y-Sp-Si($R^2$)$_n$(OSi$R^1_3$)$_{(3-n)}$ are
3-acryloxypropyltris(trimethylsiloxy)silane,
3-methacryloxypropyltris(trimethylsiloxy)silane,
3-methacryloxypropyltris(dimethylphenylsiloxy)silane,
1-methacryloxymethyltris(trimethylsiloxy)silane,
1-methacryloxymethylbis(trimethylsiloxy)methylsilane, and
vinyltris(trimethylsiloxy)silane.

Examples of monohydroxysilane impurities P—Y-Sp-Si($R^2$)$_n$(OH)(OSi$R^1_3$)$_{(2-n)}$ are
3-acryloxypropylbis(trimethylsiloxy)silanol,
3-methacryloxypropylbis(trimethylsiloxy)silanol,
3-methacryloxypropylbis(dimethylphenylsiloxy)silanol,
1-methacryloxymethylbis(trimethylsiloxy)silanol,
1-methacryloxymethyl(trimethylsiloxy)methylsilanol, and
vinylbis(trimethylsiloxy)silanol.

Examples of monoorganoxysilane impurities P—Y-Sp-Si($R^2$)$_n$(O$R^3$)(OSi$R^1_3$)$_{(2-n)}$ are
3-acryloxypropylbis(trimethylsiloxy)methoxysilane,
3-methacryloxypropylbis(trimethylsiloxy)methoxysilane,
3-methacryloxypropylbis(dimethylphenylsiloxy)methoxysilane,
1-methacryloxymethylbis(trimethylsiloxy)methoxysilane,
1-methacryloxymethyl(trimethylsiloxy)methylmethoxysilane and
vinylbis(trimethylsiloxy)methoxysilane.

Examples of impurities with difunctional disiloxanes of the formula [P—Y-Sp-Si($R^2$)$_n$(OSi$R^1_3$)$_{(2-n)}$]$_2$O are
1,3-bis(3-acryloxypropyl)-1,1,3,3-tetra(trimethylsiloxy) disiloxane,
1,3-bis(3-methacryloxypropyl)-1,1,3,3-tetra(trimethylsiloxy)disiloxane,
1,3-bis(1-methacryloxymethyl)-1,1,3,3-tetra(trimethylsiloxy)disiloxane,
1,3-bis(1-methacryloxypropyl)-1,1,3,3-tetra(dimethylphenylsiloxy)disiloxane,
1,3-bis(3-methacryloxypropyl)-1,3-bis(trimethylsiloxy)-1,3-dimethyldisiloxane and
1,3-divinyl-1,1,3,3-tetra(trimethylsiloxy)disiloxane.

The method according to the invention is described in more detail below:

(a) In a first step, disiloxanes (1) of the formula ($R^1$)$_3$SiOSi($R^1$)$_3$ are initially introduced in the presence of acetic acid (2) and acidic catalyst (3). The quantitative molar ratio of disiloxane (1) and alkoxysilane (4) is preferably 0.5 to 1.0 mol, preferably 0.6 to 0.8 mol, of disiloxane (1) per mole of alkoxy group of the alkoxysilane (4).

The quantitative molar ratio between acetic acid (2) and alkoxysilane (4) is preferably 1.5 to 6 mol, preferably 2 to 4 mol of acetic acid (2) per mole of alkoxysilane (4).

The acidic catalyst (3) permits the reaction with the subsequently added alkoxysilane (4). Acidic catalysts which can be used are, for example, concentrated hydrochloric acid, sulfuric acid, trifluoroacetic acid or trifluoromethanesulfonic acid, but also Lewis acids, such as AlCl$_3$ or TiCl$_3$, provided they do not enter into any secondary reaction with further substituents of the alkoxysilane. Typically, 0.001 to 0.01 mol of acidic catalyst (3), based on the amount of alkoxysilane, are used. The mixture is preferably heated with stirring to a temperature of from 0° C. to 60° C., more preferably 20-60° C. Higher temperatures favor secondary reactions through condensation of the alkoxysilyl groups with the formation of difunctional disiloxane.

(b) In process step (b), substituted alkoxysilanes (4) are metered in, preferably over the course of a timeframe of from 0.5 h to 3 h, more preferably 0.5 h to 2 h, and most preferably 45 min to 75 min, the temperature being kept at 0° C. to 60° C., preferably between 20 and 60° C. In order to permit the most complete prereaction possible, the mixture is post-stirred for a further 30 min to 3 h, preferably 45 min to 2 h.

(c) In order to eliminate the by-product content of monoorganoxysilane after the prereaction, acetyl chloride (5) is metered in at 0° C. to 60° C., preferably at 20° C. to 60° C. preferably in a timeframe of from 5 min to 3 h, more preferably 10 min to 2 h. The molar ratio of acetyl chloride (5) to alkoxysilane (4) is preferably 0.2 to 1.0 mol, more preferably 0.3 to 0.8 mol, based in each case on 1 mol of the alkoxysilane (4). The function of the acetyl chloride is to bind water and methanol which is formed in the course of the reaction and thus to remove them from the equilibrium. In this way, the content of monoorganosiloxane still present is ultimately minimized.

(d) An essential advantage of the method is due to the fact that after the metered addition of acetyl chloride has taken place and brief post-reaction (preferably 5 min-1 h, preferably 10 min to 30 min), the reaction mixture phase-separates. An acidic phase comprising alcohol, such as MeOH, water, acetic acid, acidic catalyst, can be separated off. This offers, first, the advantage that alcohol, such as MeOH and water are separated and thereby possible subsequent secondary reactions are prevented, and second, the amount of hexamethyldisilazane to be used for neutralization is minimized.

(e) In order to ultimately minimize the still remaining by-product content of monohydroxysilane, 0.02-1.0 mol, preferably 0.1-0.8 mol, more preferably 0.2-0.6 mol of hexamethyldisilazane (6), are added per mole of alkoxysilane (4) and then the reaction mixture stirred. The metering and post-reaction preferably takes place within a total time of 1 h-5 h, preferably at 10° C.-40° C.

A neutralization of the reaction mixture prior to distillation is essential in order to avoid, during subsequent distillation, formation of by-products anew, in particular difunctional disiloxane, due to a shift in the equilibrium under acidic conditions. Moreover, as a result of dispensing with the use of aqueous neutralizing agents when using hexamethyldisilazane, a subsequent formation of monohydroxysilane as a by-product is avoided.

(f) The resulting salts are filtered off, for example, via a pressure suction filter or centrifuge and downstream fine filtration, in which case preferably a sieve or filter, preferably with a mesh width of 0.2-2 μm, more preferably 0.2 0.5 μm, is used. In order to stabilize the product during and/or after distillation, the addition of stabilizers before or after the distillation step is possible.

The volatile constituents are separated and then the product is distilled in vacuo. For the distillation, besides conventional distillation methods with or without distillation column(s), it is also possible to use thermally gentle methods such as thin-film evaporation, short-path evaporation and the like. Furthermore, in the course of the distillation, an additional separation of inorganic impurities, e.g. salts, takes place. Besides a high purity, the exclusion of polymeric fractions is also essential both for the processing properties and also the material properties of the polymerizable silicone. In order to avoid the formation of polymer in polymerizable silicones during their synthesis, stabilizers can be added during the reaction or the work-up. On account of the inhibiting effect of oxygen with regard to a potential free-radical polymerization of acrylic groups, methacrylic groups, ethynyl groups or vinyl groups it is also possible to carry out individual process steps under an oxygen partial pressure (e.g. lean air). Additionally, the existence of polymeric impurities in the product is avoided by distilling the product. To stabilize the polymerizable silicone, stabilizers can be added for the storage also after its isolation. The content of added stabilizer here preferably should be between 100 and 5000 ppm (with reference to alkoxysilane (4)), preferably between 200 and 2000 ppm. Examples of stabilizers are 2,6-di-tert-butyl-4-methylphenol (BHT), 2,6-di-tert-butyl-4-(dimethylaminomethyl)phenol and phenothiazine.

(g) In order to separate any salts, metals, and particles that are still present, the distilled polymerizable silicone is, if appropriate, filtered again. For this, for example, a filter candle with a pore size of 0.1-1 μm, preferably 0.2-0.5 μm, is used.

The polymerizable silicones produced by the method according to the invention have a high purity of at least 98.5% and a low content of 0.4% of each of by-products monohydroxysilanes, monoorganoxysilanes and difunctional disiloxanes.

Furthermore, the polymerizable silicones produced by the method according to the invention preferably have salt contents of less than 200 ppm, more preferably less than 150 ppm.

The polymerizable silicones according to the invention are used as raw material and/or monomers for the production of electronic materials, for the production of contact lenses and optical components, as raw materials in compositions for functional and industrial coatings, for polymeric microstructures, or in cosmetics applications.

EXAMPLE 1

3-methacryloxypropyltris(trimethylsiloxy)silane

In a three-neck flask, 80.8 g (0.499 mol) of hexamethyldisiloxane, 39.9 g (0.67 mol) of acetic acid and 0.5 g of a 10% solution of trifluoromethanesulfonic acid in acetic acid (0.0003 mol) are initially introduced and heated to 45° C. with stirring. Then, over the course of one hour (at 45° C.), 55.0 g (0.22 mol) of 3-methacryloxypropyl-trimethoxysilane (WACKER GENIOSIL® GF 31) are added and after-stirred for 1 h at 45° C. The crude product is analyzed by means of gas chromatography (GC). Besides the readily volatile constituents of the reaction mixture, the following GC contents are found: product (44.3 area %); monoorganoxy impurity $CH_2=CH(CH_3)-COO-(CH_2)_3-Si(OSiMe_3)_2OMe$ (1.1 area %); monohydroxy impurity $CH_2=CH(CH_3)-COO-(CH_2)_3Si(OSiMe_3)_2OH$ (0.6 area %), and 0.5 area % of the difunctional disiloxane (dimers) $[CH_2=CH(CH_3)-COO-(CH_2)_3-Si(OSiMe_3)_2]O$.

At 45° C., 13.1 g (0.167 mol) of acetyl chloride are added to the reaction mixture (over the course of 10 min), and the mixture is after-stirred for 10 min. At room temperature, an acidic phase is separated from the organic layer before the reaction mixture is analyzed again by gas chromatography. The following are found: product (50.0 area %); monoorganoxy impurity $CH_2=CH(CH_3)-COO-(CH_2)_3Si(OSiMe_3)_2OMe$ (0.1 area %); monohydroxy impurity $CH_2=CH(CH_3)-COO-(CH_2)_3-Si(OSiMe_3)_2OH$ (0.5 area %) and 0.8 area % of the difunctional disiloxane (dimers) $[CH_2=CH(CH_3)-COO-(CH_2)_3-Si(OSiMe_3)_2]O$.

In order to eliminate/reduce the remaining content of monohydroxysilane impurity, 18 g (0.12 mol) of hexamethyldisilazane are added, the reaction mixture being neutralized at the same time. After filtering off the formed salts, the reaction mixture is again analyzed by means of GC. The following are found: product (44.6 area %); monoorganoxy impurity $CH_2=CH(CH_3)-COO-(CH_2)_3-Si(OSiMe_3)_2OMe$ (0.1 area %); monohydroxy impurity $CH_2=CH(CH_3)-COO-(CH_2)_3-Si(OSiMe_3)_2OH$ (0.0 area %) and 0.8 area % of the difunctional disiloxane (dimers) $[CH_2=CH(CH_3)-COO-(CH_2)_3-Si(OSiMe_3)_2]O$.

After distilling off the volatile constituents, the product is distilled in vacuo and filtered off via a filter candle. The desired product is obtained in a yield of 80% and has a purity of 99.6 area % (contains 0.1 area % monoorganoxysilane). The specified monohydroxy and disiloxane impurities can no longer be detected.

COMPARATIVE EXPERIMENT 1

The process is carried out analogously to example 1 except that following the addition of methacryloxypropyltri-methoxysilane (WACKER GENIOSIL® GF 31) and corresponding post-stirring, 17.0 g (0.167 mol) of acetic anhydride are added instead of acetyl chloride and that instead of a reaction and neutralization with hexamethyldisilazane, neutralization is carried out with $CaCO_3$.

Following the addition of methacryloxypropyltrimethoxysilane (WACKER GENIOSIL® GF 31) and corresponding after-stirring, the crude product is firstly analyzed by means of gas chromatography (GC). Besides the readily volatile constituents of the reaction mixture, the following GC contents are found: product (45.8 area %); monoorganoxy impurity $CH_2=CH(CH_3)—COO—(CH_2)_3—Si(OSiMe_3)_2OMe$ (1.2 area %); monohydroxy impurity $(CH_2=CH(CH_3)—COO—(CH_2)_3—Si(OSiMe_3)_2OH$ (0.6 area %) and 0.5 area % of the difunctional disiloxane (dimers) $[CH_2=CH(CH_3)—COO—(CH_2)_3—Si(OSiMe_3)_2]O$.

Following the addition of the acetic anhydride (17.0 g; 0.167 mol), however, in contrast to example 1) according to the invention, no acidic lower phase can be separated off. The reaction mixture is analyzed again by gas chromatography. The following are found (besides the readily volatile constituents) product (48.6 area %); monoorganoxy impurity $CH_2=CH(CH_3)—COO—(CH_2)_3—Si(OSiMe_3)_2OMe$ (0.6 area %); monohydroxy impurity $CH_2=CH(CH_3)—COO—(CH_2)_3—Si(OSiMe_3)_2OH$ (0.4 area %) and 0.8 area % of the difunctional disiloxane (dimers) $[CH_2=CH(CH_3)—COO—(CH_2)_3—Si(OSiMe_3)_2]O$.

The reaction is stopped or neutralized by adding 60 g of $CaCO_3$, the viscosity of the reaction mixture increasing significantly on account of the introduction of solid. In the gas chromatographic analysis, the following are found besides the readily volatile constituents: product (46.2 area %); monoorganoxy impurity $CH_2=CH(CH_3)—COO—(CH_2)_3—Si(OSiMe_3)_2OMe$ (0.7 area %); monohydroxy impurity $CH_2=CH(CH_3)—COO—(CH_2)_3—Si(OSiMe_3)_2OH$ (0.5 area %) and 0.8 area % of the difunctional disiloxane (dimers) $[CH_2=CH(CH_3)—COO—(CH_2)_3—Si(OSiMe_3)_2]O$.

After filtering off the salts and distilling off the volatile constituents, the reaction mixture is analyzed by means of GC. The following are found: product (96.4 area %); monoorganoxy impurity $CH_2=CH(CH_3)—COO—(CH_2)_3—Si(OSiMe_3)_2OMe$ (1.2 area %); monohydroxy impurity $CH_2=CH(CH_3)—COO—(CH_2)_3—Si(OSiMe_3)_2OH$ (0.8 area %) and 1.2 area % of the difunctional disiloxane (dimers) $[CH_2=CH(CH_3)—COO—(CH_2)_3—Si(OSiMe_3)_2]O$.

Following vacuum distillation and fine filtration, the product is obtained in a yield of 62%, and has the following purities: product (97.4 area %); monoorganoxy impurity $CH_2=CH(CH_3)—COO—(CH_2)_3—Si(OSiMe_3)_2OMe$ (1.1 area %); monohydroxy impurity $(CH_2=CH(CH_3)—COO—(CH_2)_3—Si(OSiMe_3)_2OH$ (0.9 area %) and 0.0 area % of the difunctional disiloxane (dimers) $[CH_2=CH(CH_3)—COO—(CH_2)_3—Si(OSiMe_3)_2]O$.

COMPARATIVE EXPERIMENT 2

The process is carried out analogously to example 1 except that instead of a reaction and neutralization with hexamethyldisilazane, neutralization is carried out with $CaCO_3$.

After adding methacryloxypropyltrimethoxysilane (WACKER GENIOSIL® GF 31) and corresponding after-stirring, the crude product is firstly investigated by means of gas chromatography (GC). Besides the readily volatile constituents of the reaction mixture, the following GC contents are found: product (46.3 area %); monoorganoxy impurity $CH_2=CH(CH_3)—COO—(CH_2)_3—Si(OSiMe_3)_2OMe$ (1.3 area %); monohydroxy impurity $CH_2=CH(CH_3)—COO—(CH_2)_3—Si(OSiMe_3)_2OH$ (0.7 area %) and 0.4 area % of the difunctional disiloxane (dimers) $[CH_2=CH(CH_3)—COO—(CH_2)_3—Si(OSiMe_3)_2]O$.

Following the corresponding addition of 13.1 g (0.167 mol) of acetyl chloride and after-stirring (10 min), the resulting acidic lower phase is separated off and the reaction mixture is analyzed by means of gas chromatography: product (47.3 area %); monoorganoxy impurity $CH_2=CH(CH_3)—COO—(CH_2)_3—Si(OSiMe_3)_2OMe$ (0.1 area %); monohydroxy impurity $CH_2=CH(CH_3)—COO—(CH_2)_3—Si(OSiMe_3)_2OH$ (0.5 area %) and 0.9 area % of the difunctional disiloxane (dimers) $[CH_2=CH(CH_3)—COO—(CH_2)_3—Si(OSiMe_3)_2]O$.

The reaction is stopped or neutralized by adding 10 g of $CaCO_3$.

In the gas chromatographic analysis, the following are found besides the readily volatile constituents: product (47.7 area %); monoorganoxy impurity $CH_2=CH(CH_3)—COO—(CH_2)_3—Si(OSiMe_3)_2OMe$ (0.1 area %); monohydroxy impurity $CH_2=CH(CH_3)—COO—(CH_2)_3—Si(OSiMe_3)_2OH$ (0.6 area %) and 0.7 area % of the difunctional disiloxane (dimers) $[CH_2=CH(CH_3)—COO—(CH_2)_3—Si(OSiMe_3)_2]O$.

After separating off the salts and distilling off the readily volatile constituents, the crude product is obtained in the following purity: product (97.2 area %); monoorganoxy impurity $CH_2=CH(CH_3)—COO—(CH_2)_3—Si(OSiMe_3)_2OMe$ (0.2 area %); monohydroxy impurity $CH_2=CH(CH_3)—COO—(CH_2)_3—Si(OSiMe_3)_2OH$ (0.9 area %) and 1.3 area % of the difunctional disiloxane (dimers) $[CH_2=CH(CH_3)—COO—(CH_2)_3—Si(OSiMe_3)_2]O$.

Following distillation in vacuo and fine filtration, the product is obtained with a yield of 60%. It has the following purity (GC area %): product (98.1 area %); monoorganoxy impurity $CH_2=CH(CH_3)—COO—(CH_2)_3—Si(OSiMe_3)_2OMe$ (0.2 area %); monohydroxy impurity $CH_2=CH(CH_3)—COO—(CH_2)_3—Si(OSiMe_3)_2OH$ (1.1 area %)

TABLE

|  | Example 1 | Comparison 1 | Comparison 2 |
|---|---|---|---|
| After reaction |  |  |  |
| Content of monoorganoxy | 1.1% | 1.2% | 1.3% |
| Content of monohydroxy | 0.6% | 0.6% | 0.7% |
| Content of disiloxane | 0.5% | 0.5% | 0.4% |
| Content of product | 44.3% | 45.8% | 46.3% |
| Post-reaction with | acetyl chloride | acetic anhydride | acetyl chloride |
| Molar ratio [AcCl/alkoxysilanes] or [Ac$_2$O/alkoxysilane] | 0.75 | 0.75 | 0.75 |
| Removal of acidic phase | + | not possible | + |
| Content of monoorganoxy | 0.1% | 0.6% | 0.1% |
| Content of monohydroxy | 0.5% | 0.4% | 0.5% |
| Content of disiloxane | 0.8% | 0.8% | 0.9% |
| Content of product | 50.0% | 48.6% | 47.3% |
| Neutralization | HMN | CaCO$_3$ | CaCO$_3$ |
| Molar ratio [HMN/alkoxysilane] or [CaCO$_3$/alkoxysilane] | 0.5 | 2.7 | 0.45 |
| Content of monoorganoxy | 0.1% | 0.7% | 0.1% |
| Content of monohydroxy | 0.0% | 0.5% | 0.6% |
| Content of disiloxane | 0.8% | 0.8% | 0.7% |
| Content of product | 44.6% | 46.2% | 47.7% |
| Product after distilling off the low-boiling component |  |  |  |
| Content of monoorganoxy | 0.1% | 1.2% | 0.2% |
| Content of monohydroxy | 0.0% | 0.8% | 0.9% |
| Content of disiloxane | 1.3% | 1.2% | 1.3% |
| Content of product | 98.4% | 96.4% | 97.2% |
| End product after distillation and filtration |  |  |  |
| Content of monoorganoxy | 0.1% | 1.1% | 0.2% |
| Content of monohydroxy | 0.0% | 0.9% | 1.1% |
| Content of disiloxane | 0.0% | 0.0% | 0.0% |
| Content of product | 99.6% | 97.4% | 98.1% |
| Yield | 80% | 62% | 60% |

EXAMPLE 2

1-methacryloxymethyltris(trimethylsiloxy)silane

In a three-necked flask, 80.8 g (0.499 mol) of hexamethyldisiloxane, 39.9 g (0.67 mol) of acetic acid and 0.5 g of a 10% strength solution of trifluoromethane-sulfonic acid in acetic acid (0.0003 mol) are initially introduced and heated to 45° C. with stirring. Then, over the course of one hour (at 45° C.), 48.8 g (0.22 mol) of 1-methacryloxymethyltrimethoxysilane (WACKER GENIOSIL® XL 33) are added and after-stirred for 1 h at 45° C. The crude product is analyzed by means of gas chromatography (GC). Besides the readily volatile constituents of the reaction mixture, the following GC contents are found: product (44.7 area %); monoorganoxy impurity ($CH_2$=$CH(CH_3)$—COO—$CH_2$—Si($OSiMe_3$)$_2$OMe, 1.1 area %); monohydroxy impurity ($CH_2$=$CH(CH_3)$—COO—$CH_2$—Si($OSiMe_3$)$_2$OH, 0.7 area %) and 0.6 area % of the difunctional disiloxane (dimers) [$CH_2$=$CH(CH_3)$—COO—($CH_2$)$_3$—Si($OSiMe_3$)$_2$]O. At 40° C., 6.1 g (0.078 mol) of acetyl chloride are added to the reaction mixture and then the mixture is after-stirred for 20 min. At room temperature, an acidic lower phase of the organic layer is separated off before the reaction mixture is analyzed again by gas chromatography. The following are found: product (49.3 area %); monoorganoxy impurity ($CH_2$=$CH(CH_3)$—COO—$CH_2$—Si($OSiMe_3$)$_2$OMe, 0.2 area %); monohydroxy impurity ($CH_2$=$CH(CH_3)$—COO—$CH_2$—Si($OSiMe_3$)$_2$OH, 0.7 area %) and 0.9 area % of the difunctional disiloxane (dimers) [$CH_2$=$CH(CH_3)$—COO—$CH_2$—Si($OSiMe_3$)$_2$]O.

In order to eliminate/reduce the remaining content of monohydroxysilane impurity, 17.9 g (0.11 mol) of hexamethyldisilazane are added, the reaction mixture being neutralized at the same time. After filtering off the formed salt, the reaction mixture is analyzed again by means of GC. The following are found (besides readily volatile constituents): product 48.7 area %; monoorganoxy impurity ($CH_2$=$CH(CH_3)$—COO—$CH_2$—Si($OSiMe_3$)$_2$OMe, 0.2 area %); monohydroxy impurity ($CH_2$=$CH(CH_3)$—COO—$CH_2$—Si($OSiMe_3$)$_2$OH, 0.0 area %) and 0.9 area % of the difunctional disiloxane (dimers) [$CH_2$=$CH(CH_3)$—COO—$CH_2$—Si($OSiMe_3$)$_2$]O. After distilling off the volatile constituents, the product is distilled in vacuo and filtered off over a filter candle (pore width 0.2 μm). The desired product is obtained in a yield of 78% and has a purity of 99.3 area % (also comprises 0.2 area % monoorganoxysilane). The monohydroxy impurity can no longer be detected).

EXAMPLE 3

1-methacryloxymethylbis(trimethylsiloxy)-methylsilane

The procedure is analogous to example 2. Instead of 48.8 g (0.22 mol) of 1-methacryloxymethyltrimethoxysilane (WACKER GENIOSIL® XL 33), in the present example 44.9 g (0.22 mol) of 1-methacryloxymethyldimethoxymethylsilane (WACKER GENIOSIL® XL 32) and only 56.7 g (0.35 mol) of hexamethyl-disiloxane are used. The desired product is obtained in a yield of 81%. GC purity: 99.4% of 1-methacryloxymethyl-bis(trimethylsiloxy)methylsilane (0.1 area % of mono-organoxysilane). The monohydroxy impurity can no longer be detected.

EXAMPLE 4

Vinyltris(trimethylsiloxy)silane

The procedure is analogous to example 2. Instead of 48.8 g (0.22 mol) of 1-methacryloxymethyltrimethoxysilane (WACKER GENIOSIL® XL 33), in the present example 32.6 g (0.22 mol) of vinyltrimethoxysilane are used. The desired product is obtained in a yield of 79%. GC purity: 99.6% of vinyl-tris(trimethylsiloxy)silane (0.2 area % of mono-organoxysilane). The monohydroxy impurity can no longer be detected.

The invention claimed is:

1. A process for the production of polymerizable silicones of the formula

comprising:
(a) providing a mixture of disiloxane (1) of the formula

acetic acid (2) and an acid catalyst (3),
(b) metering in and reacting at a temperature of from 0° to 60° C. a substituted alkoxysilane (4) of the formula

(c) adding 0.2-1.0 mol of acetyl chloride (5), based on 1 mol of alkoxysilane (4),
(d) following a phase separation, separating an acid phase from a product phase,
(e) adding 0.02 to 1.0 mol of hexamethyldisilazane (6), based on 1 mol of alkoxysilane (4) to the product phase,
(f) separating a salt formed in the product phase, removing readily volatile constituents from the product phase and distilling the product phase to recover a distilled product, and optionally
(g) filtering the distilled product,
where
$R^1$ each are identical or different and are hydrogen or optionally substituted monovalent hydrocarbon radicals having 1 to 18 carbon atoms,
$R^2$ each are identical or different and are hydrogen or optionally substituted monovalent hydrocarbon radicals having 1 to 18 carbon atoms,
$R^3$ each are identical or different and are alkyl radicals having 1 to 18 carbon atoms optionally substituted with alkoxy groups,
Sp is a single bond or a divalent hydrocarbon radical having 1 to 8 carbon atoms,
Y is a single bond or —O—,
P is an acryloxy, methacryloxy, vinyl or allyl radical, and n is 0, 1 or 2.

2. The process of claim 1, wherein the quantitative molar ratio of disiloxane (1) and alkoxysilane (4) is 0.5 to 1.0 mol of disiloxane (1) per mole of alkoxy group of the alkoxysilane (4).

3. The process of claim 1, wherein the quantitative molar ratio of disiloxane (1) and alkoxysilane (4) is 0.6 to 0.8 mol of disiloxane (1) per mole of alkoxy group of the alkoxysilane (4).

4. The process of claim 1, wherein, in process step (b), the alkoxysilane (4) is metered in over the course of 0.5 h-3 h and the mixture is then post-reacted at 0° C.-60° C.

5. The process of claim 1, wherein the alkoxysilane (4) is 3-methacryloxypropyltrimethoxysilane.

6. The process of claim 1, wherein the disiloxane (1) used is hexamethyldisiloxane.

7. The process of claim 1, wherein a stabilizer is added to the product phase before distillation, or to the distilled product.

8. The process of claim 1, wherein at least one process step is carried out under an oxygen partial pressure.

9. The process of claim 1, wherein the polymerizable silicone product of the formula $$P\text{—}Y\text{-}Sp\text{-}Si(R^2)_n(OSiR^1{}_3)_{(3-n)} \quad (I)$$

has a purity of at least 98.5 area % as measured by gas chromatography, a content of less than 0.4 area % of difunctional disiloxane of the formula $$[P\text{—}Y\text{-}Sp\text{-}Si(R^2)_n(OSiR^1{}_3)_{(2-n)}]O,$$

of less than 0.4 area % of monohydroxysilane of the formula $$P\text{—}Y\text{-}Sp\text{-}Si(R^2)_n(OH)(OSiR^1{}_3)_{(2-n)}$$

and less than 0.4 area % of monoorganoxysilane of the formula $$P\text{—}Y\text{-}Sp\text{-}Si(R^2)_n(OR^3)(OSiR^1{}_3)_{(2-n)},$$

where $R^1$ each are identical or different and are hydrogen or optionally substituted monovalent hydrocarbon radicals having 1 to 18 carbon atoms, $R^2$ each are identical or different and are hydrogen or optionally substituted monovalent hydrocarbon radicals having 1 to 18 carbon atoms, $R^3$ each are identical or different and are alkyl radicals having 1 to 18 carbon atoms optionally substituted with alkoxy groups, Sp is a single bond or a divalent hydrocarbon radical having 1 to 8 carbon atoms, Y is a single bond or —O—, P is an acryloxy, methacryloxy, vinyl or allyl radical, and n is 0, 1 or 2.

10. The process of claim 9, wherein the polymerizable silicone product has a purity of at least 99.0 area %, a content of difunctional disiloxane of less than 0.2 area %, a content of monohydroxysilane of less than 0.3 area %, and a content of monoalkoxysilane of less than 0.3 area %.

* * * * *